(12) United States Patent
Morita et al.

(10) Patent No.: US 8,529,926 B2
(45) Date of Patent: Sep. 10, 2013

(54) PESTICIDAL COMPOSITIONS

(75) Inventors: Masayuki Morita, Osaka (JP); Takao Awazu, Kusatsu (JP); Akira Nakagawa, Kusatsu (JP); Taku Hamamoto, Kusatsu (JP)

(73) Assignee: Ishihara Sangyo Kaisha, Ltd., Osaka-shi (JP)

( * ) Notice: Subject to any disclaimer, the term of this patent is extended or adjusted under 35 U.S.C. 154(b) by 0 days.

(21) Appl. No.: 12/867,854

(22) PCT Filed: Mar. 11, 2009

(86) PCT No.: PCT/JP2009/055214
§ 371 (c)(1),
(2), (4) Date: Aug. 16, 2010

(87) PCT Pub. No.: WO2009/113712
PCT Pub. Date: Sep. 17, 2009

(65) Prior Publication Data
US 2010/0317700 A1 Dec. 16, 2010

(30) Foreign Application Priority Data

Mar. 13, 2008 (JP) ................. 2008-063782
Nov. 28, 2008 (JP) ................. 2008-305084

(51) Int. Cl.
*A01N 25/00* (2006.01)
*A01N 43/56* (2006.01)

(52) U.S. Cl.
USPC ............................ 424/409; 424/405; 514/341

(58) Field of Classification Search
USPC ........................................... 514/531
See application file for complete search history.

(56) References Cited

U.S. PATENT DOCUMENTS

| 7,612,100 | B2 * | 11/2009 | Koyanagi et al. | 514/341 |
| 7,994,201 | B2 * | 8/2011 | Koyanagi et al. | 514/341 |
| 2007/0129407 | A1 | 6/2007 | Koyanagi et al. | |
| 2008/0027046 | A1 | 1/2008 | Annan et al. | |
| 2008/0275065 | A1 | 11/2008 | O'Sullivan et al. | |
| 2008/0305093 | A1 | 12/2008 | Gutsche et al. | |
| 2009/0133318 | A1 | 5/2009 | Lahm | |
| 2010/0028304 | A1 | 2/2010 | Koyanagi et al. | |
| 2010/0035935 | A1 | 2/2010 | Koyanagi et al. | |
| 2010/0130358 | A1 | 5/2010 | Muehlebach et al. | |
| 2011/0130427 | A1 * | 6/2011 | Hamamoto | 514/341 |
| 2011/0257231 | A1 * | 10/2011 | Koyanagi et al. | 514/341 |

FOREIGN PATENT DOCUMENTS

| KZ | 18197 A | | 1/2007 |
| RU | 2 147 179 C1 | | 4/2000 |
| WO | 2005 077934 | | 8/2005 |
| WO | WO2005/077934 | * | 8/2005 |
| WO | 2005 118552 | | 12/2005 |
| WO | 2006 007595 | | 1/2006 |
| WO | 2006 040113 | | 4/2006 |
| WO | 2006 055922 | | 5/2006 |
| WO | 2006 080311 | | 8/2006 |
| WO | WO2006108552 | * | 10/2006 |
| WO | 2007 020877 | | 2/2007 |
| WO | 2007 080131 | | 7/2007 |
| WO | 2007 081553 | | 7/2007 |
| WO | 2008 064891 | | 6/2008 |
| WO | 2008 072783 | | 6/2008 |
| WO | 2010 010958 | | 1/2010 |

OTHER PUBLICATIONS

U.S. Appl. No. 13/003,895, filed Jan. 13, 2011, Hamamoto.
U.S. Appl. No. 12/919,428, filed Aug. 25, 2010, Morita, et al.
Egyptian Office Action issued Oct. 2, 2012, in Patent Application No. PCT2010091505 (with English-language translation) Ax Ay.
Kazakhstan Office Action issued Aug. 15, 2012, in Kazakhstan Patent Application No. 2010/1615.1 (9445/RU-GR) (with English translation).

* cited by examiner

*Primary Examiner* — Neil Levy
(74) *Attorney, Agent, or Firm* — Oblon, Spivak, McClelland, Maier & Neustadt, L.L.P.

(57) ABSTRACT

To provide a formulation composition which improves the controlling effect of an anthranilamide compound against pests. A pesticide composition which is a concentrated composition containing an anthranilamide compound as a pesticidal active ingredient, a dispersant and a hydrophilic organic solvent, characterized in that when the composition is diluted with water, the anthranilamide compound precipitates as solid particles in water.

11 Claims, 1 Drawing Sheet

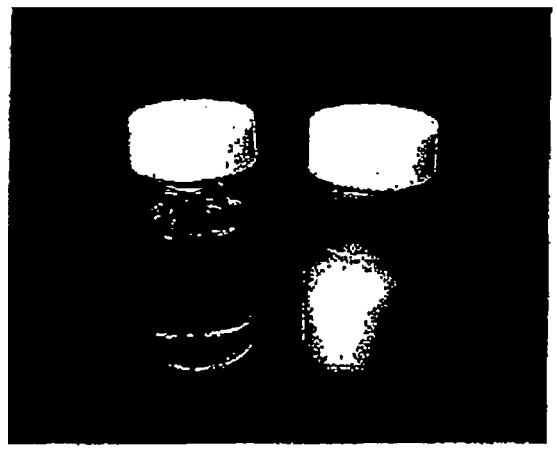
The left sample containing compound (1) of the composition according to the present invention completely dissolves to form a colorless and transparent liquid, whereas the right sample containing the compound (1) of the formulation of Koyanagi's Formulation Example 3, results in a suspended solution.

PESTICIDAL COMPOSITIONS

TECHNICAL FIELD

The present invention relates to a pesticidal composition comprising an anthranilamide compound of which the pesticidal activity is improved.

BACKGROUND ART

It has been known that anthranilamide type insecticides are useful for controlling pests such as Lepidoptera, and Patent Document 1 discloses as its formulations, various formulations such as an emulsifier, is a wettable powder, a dust or granules. Further, Patent Document 2 discloses as a formulation which improves the effect of the compound for controlling pests, an oily suspension containing a hydrophobic solvent.

Patent Document 1: WO2005/077934
Patent Document 2: WO2007/081553

DISCLOSURE OF THE INVENTION

Problems to be Solved by the Invention

Many pesticides including anthranilamide type compounds have characteristic spectrums and effects respectively, but have some problems that the effects are sometimes inadequate to certain pests, that their residual activities are sometimes poor and the effects are not satisfactorily maintained for a certain period of time, and that adequate pesticidal effects cannot be practically achieved. Therefore, it has been desired to improve the controlling effects by a formulation method.

Means of Solving the Problems

The present inventors have conducted various studies to solve the above problems, and as a result found that the controlling effects against pests are remarkably improved by dissolving an anthranilamide compound with a dispersant in a hydrophilic organic solvent and diluted with water, followed by applying it. Thus, the present invention has been accomplished. The composition of the present invention is a concentrated composition wherein an anthranilamide compound and a dispersant are dissolved in a hydrophilic organic solvent, and when the composition is diluted with water, the anthranilamide compound uniformly precipitates as fine solid particles in water, whereby a suspended spray liquid can be easily prepared.

That is, the present invention relates to a pesticide composition which is a concentrated composition containing an anthranilamide compound as a pesticidal active ingredient, a dispersant and a hydrophilic organic solvent, characterized in that when the composition is diluted with water, the anthranilamide compound precipitates as solid particles in water.

Effect of the Invention

The composition of the present invention makes it possible to improve the effects of the anthranilamide compound and to control pests with a low dose of the compound.

BEST MODE FOR CARRYING OUT THE INVENTION

The composition of the present invention is a concentrated composition, and after diluted with water in an amount of from 5 to 100,000 times usually, the composition of the present invention is sprayed.

The composition of the present invention contains at least one anthranilamide compound. The anthranilamide compound used in the present invention may, for example, be an anthranilamide compound represented by formula (I):

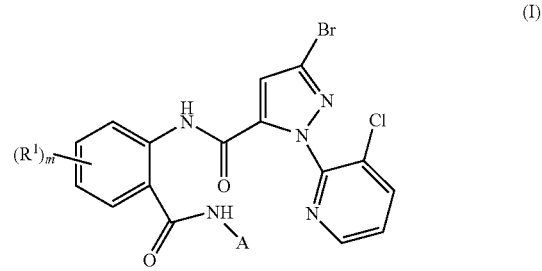

wherein $R^1$ is halogen, alkyl or cyano, A is alkyl which may be substituted by $C_{3-4}$ cycloalkyl, and m is from 0 to 4.

In the formula (I), the alkyl or the alkyl moiety of $R^1$ and A may be linear or branched. As a specific example, $C_{1-6}$ alkyl such as methyl, ethyl, propyl, isopropyl, butyl, pentyl or hexyl may be mentioned.

Further, the halogen as $R^1$ may, for example, be each atom of fluorine, chlorine or bromine.

The anthranilamide compound is preferably the following compounds.

(1) 3-Bromo-N-(2-bromo-4-chloro-6-(1-cyclopropylethylcarbamoyl)phenyl)-1-(3-chloropyridin-2-yl)-1H-pyrazol-5-carboxamide (Compound 1)

(2) 3-Bromo-N-(4-chloro-2-(1-cyclopropylethylcarbamoyl)-6-methylphenyl)-1-(3-chloropyridin-2-yl)-1H-pyrazol-5-carboxamide (Compound 2)

(3) 3-Bromo-N-(2-bromo-4-chloro-6-(cyclopropylmethylcarbamoyl)phenyl)-1-(3-chloropyridin-2-yl)-1H-pyrazol-5-carboxamide (Compound 3)

(4) 3-Bromo-N-(4-chloro-2-methyl-6-(methylcarbamoyl)phenyl)-1-(3-chloropyridin-2-yl)-1H-pyrazol-5-carboxamide (Compound 4)

(5) 3-Bromo-1-(3-chloropyridin-2-yl)-N-(4-cyano-2-methyl-6-(methylcarbamoyl)phenyl)-1H-pyrazol-5-carboxamide (Compound 5)

The content of the anthranilamide compound in the composition is from 0.1 to 45 wt %, preferably from 1 to 20 wt %.

Further, in addition to the anthranilamide compound, another pesticide may be added to the composition of the present invention. Such another pesticide may, for example, be an insecticide, a miticide, a nematocide, a soil pesticide or a fungicide.

As the dispersant used in the present invention, at least one surfactant selected from the group consisting of a nonionic surfactant and an anionic surfactant may be used.

As the nonionic surfactant used in the present invention, the following surfactants may be mentioned.

Polyoxyalkylene surfactant: A polyoxyalkylene alkyl ether, a $C_{8-18}$ polyoxyethylene alkyl ether, an ethylene oxide adduct of alkylnaphthol, a $C_{8-12}$ polyoxyethylene alkyl aryl ether, a polyoxyethylene (mono, di or tri)phenyl phenyl ether, a polyoxyethylene (mono, di or tri)benzyl phenyl ether, a polyoxypropylene (mono, di or tri)benzyl phenyl ether, a polyoxyethylene (mono, di or tri)styrylphenyl ether, a polyoxypropylene (mono, di or tri)styrylphenyl ether, a polymer of a polyoxyethylene (mono, di or tri)styrylphenyl ether; a polyoxyethylene polyoxypropylene block polymer, a $C_{8-18}$ alkyl polyoxyethylene polyoxypropylene block polymer ether, a $C_{8-12}$ alkyl phenylpolyoxyethylene polyoxypropylene block polymer ether, a polyoxyethylene bisphenyl ether, a polyoxyethylene resin acid ester, a $C_{8-18}$ polyoxyethylene aliphatic acid monoester, a $C_{8-18}$ polyoxyethylene aliphatic acid diester, a $C_{8-18}$ polyoxyethylene sorbitan aliphatic acid ester, a glycerol aliphatic acid ester ethylene oxide adduct, a castor oil ethylene oxide adduct, a cured castor oil ethylene oxide adduct, a $C_{8-18}$ alkylamine ethylene oxide adduct or a $C_{8-18}$ aliphatic acid amide ethylene oxide adduct may, for example, be mentioned.

Polyhydric alcohol surfactant: A glycerol aliphatic acid ester, a polyglycerol aliphatic acid ester, a pentaerythritol aliphatic acid ester, a $C_{8-18}$ sorbitol aliphatic acid ester, a $C_{8-18}$ sorbitan aliphatic acid ester, a sucrose aliphatic acid ester, a polyhydric alcohol alkyl ether, an aliphatic acid alkanolamide, an alkyl glycoxide or an alkyl polyglycoside may, for example, be mentioned.

Among the above nonionic surfactants, preferred are the $C_{8-12}$ polyoxyethylene alkyl aryl ether and the polyoxyethylene tristyrylphenyl ether.

As the anionic surfactant, the following surfactants may be mentioned.

Carboxylic acid surfactant: A copolymer of an olefin (for example, isobutylene or diisobutylene) with a polyacrylic acid, a polymethacrylic acid, a polymaleic acid, a polymaleic acid anhydride, maleic acid or maleic acid anhydride; a copolymer of acrylic acid with itaconic acid; a copolymer of methacrylic acid with itaconic acid; a copolymer of styrene with maleic acid or maleic acid anhydride; a copolymer of acrylic acid with methacrylic acid; a copolymer of acrylic acid with methyl acrylate; a copolymer of acrylic acid with a vinyl acetate; a copolymer of acrylic acid with maleic acid or maleic acid anhydride; a $C_{12-18}$ N-methyl aliphatic acid sarcocinate, a carboxylic acid such as a resin acid or a $C_{12-18}$ aliphatic acid; or a salt of such carboxylic acid may, for example, be mentioned.

Sulfuric acid ester surfactant: A $C_{12-18}$ alkyl sulfuric acid ester, a $C_{12-18}$ polyoxyethylene alkyl ether sulfuric acid ester, a $C_{12-18}$ polyoxyethylene (mono or di)alkyl phenyl ether sulfuric acid ester, a $C_{8-12}$ polyoxyethylene (mono or di) alkyl phenyl ether polymer sulfuric acid ester, a polyoxyethylene (mono, di or tri)phenyl phenyl ether sulfuric acid ester, a polyoxyethylene (mono, di or tri)benzylphenyl ether sulfuric acid ester, a polyoxyethylene (mono, di or tri)styrylphenyl ether sulfuric acid ester, a is polyoxyethylene (mono, di or tri)styrylphenyl ether polymer sulfuric acid ester, a polyoxyethylene polyoxypropylene block polymer sulfuric acid ester, a sulfated oil, a sulfated aliphatic acid ester, a sulfuric acid ester such as sulfated aliphatic acid or sulfated olefin or a salt of such sulfuric acid ester may, for example, be mentioned.

Sulfonic acid surfactant: A $C_{12-22}$ paraffin sulfonic acid, a $C_{8-12}$ alkyl aryl sulfonic acid, a $C_{8-12}$ alkylbenzene sulfonic acid, a formaldehyde condensate of a $C_{8-12}$ alkylbenzene sulfonic acid, a formaldehyde condensate of cresol sulfonic acid, a $C_{14-16}$ α-olefin sulfonic acid, a $C_{8-12}$ dialkyl sulfosuccinic acid, lignin sulfonic acid, a $C_{8-12}$ polyoxyethylene (mono or di)alkyl phenyl ether sulfonic acid, a $C_{12-18}$ polyoxyethylene alkyl ether sulfosuccinic acid half ester, a naphthalene sulfonic acid, a $C_{1-6}$ (mono or di)alkyl naphthalene sulfonic acid, a formaldehyde condensate of naphthalene sulfonic acid, a formaldehyde condensate of a (mono or di) ($C_{1-6}$) alkyl naphthalene sulfonic acid, a formaldehyde condensate of creosote oil sulfonic acid, a $C_{8-12}$ alkyl diphenyl ether disulfonic acid, sulfonic acid such as a copolymer of methacrylic acid with a polystyrene sulfonic acid and styrene sulfonic acid, or a salt of such sulfonic acid may, for example, be mentioned.

Phosphoric acid ester surfactant: A $C_{8-12}$ alkyl phosphoric acid ester, a $C_{8-18}$ polyoxyethylene alkyl ether phosphoric acid ester, a $C_{8-12}$ polyoxyethylene (mono or di)alkyl phenyl ether phosphoric acid ester, a $C_{8-12}$ polyoxyethylene (mono, di or tri)alkyl phenyl ether polymer phosphoric acid ester, a polyoxyethylene (mono, di or tri)phenyl phenyl ether phosphoric acid ester, a polyoxyethylene (mono, di or tri)benzyl phenyl ether phosphoric acid ester, a polyoxyethylene (mono, di or tri)styrylphenyl ether phosphoric acid ester, a polyoxyethylene (mono, di or tri)styrylphenyl ether polymer phosphoric acid ester, a polyoxyethylene polyoxypropylene block polymer phosphoric acid ester, a phosphatidylcholine, a phosphatidylethanolimine or a phosphoric acid condensate (such as tripolyphosphoric acid) or a salt of such phosphoric acid ester may, for example, be mentioned.

The salt of the anionic surfactant may, for example, be an alkali metal (such as lithium, sodium or potassium), an alkaline earth metal (such as calcium or magnesium), ammonium or each amine (such as alkylamine, cycloalkylamine or alkanolamine).

Among the above anionic surfactants, the $C_{8-12}$ alkylbenzene sulfonic acid and the $C_{8-18}$ polyoxyethylene alkyl ether phosphoric acid ester are preferred.

The content of the dispersant in the composition is from 0.1 to 40 wt %, preferably from 0.5 to 20 wt %.

As the hydrophilic organic solvent to be used in the present invention, any solvent can be used so long as it can dissolve the compound of the above formula (I) and can be miscible with water. Here, "dissolve" means that at least 1% of the compound of the above formula (I) dissolves, and "miscible with water" means that it can dissolve in water in an amount of 100 times. The hydrophilic organic solvent may, for example, be N,N-dimethylacetamide, dimethylformamide, dimethylsulfoxide, cyclohexanone, γ-butyrolactone, N-methyl-2-pyrrolidone, N-octyl-2-pyrrolidone, N-dodecyl-2-pyrrolidone, tetrahydroxyfurfuryl alcohol or propylene glycol monomethyl ether. It is preferably N,N-dimethylacetamide, dimethylsulfoxide, γ-butyrolactone, N-methyl-2-pyrrolidone or cyclohexanone. Such a solvent may be used alone, or two or more solvents may be used as a mixture in the composition of the present invention.

As the case requires, the composition of the present invention may contain a dispersion stabilizer, an excitation reductant or the like.

The dispersion stabilizer may, for example, be polyvinylpyrrolidone, methoxypolyethylene oxide methacrylate, polyvinyl alcohol, or a water soluble polymer such as crystallized cellulose. The excitation to reductant may, for example, be polyvinylpyrrolidone or an Arabic rubber. The dispersion stabilizer or excitation reductant may be contained in an amount of from 0.1 to 20 wt % respectively in the composition.

Further, the composition of the present invention is preferably the following ones.

(1) A composition which contains an anthranilamide compound; as a dispersant, a nonionic surfactant and/or an anionic surfactant; and at least one hydrophilic organic solvent selected from the group consisting of N,N-dimethylacetamide, dimethylsulfoxide, γ-butyrolactone, N-methyl-2-pyrrolidone and cyclohexanone.

(2) A composition which contains an anthranilamide compound; at least one dispersant selected from the group consisting of a $C_{8-12}$ polyoxyethylene alkyl aryl ether, a polyoxyethylene tristyrylphenyl ether, a $C_{8-12}$ alkylbenzene sulfonate and a $C_{8-18}$ polyoxyethylene alkyl ether phosphoric acid ester; and at least one hydrophilic organic solvent selected from the group consisting of N,N-dimethylacetamide, dimethylsulfoxide, γ-butyrolactone, N-methyl-2-pyrrolidone and cyclohexanone.

(3) The composition according to the above (1) or (2), which contains from 0.1 to 45 wt % of the anthranilamide compound, from 0.1 to 40 wt % of the dispersant and from 99.8 to 15 wt % of the hydrophilic organic solvent.

(4) The composition according to the above (3), which contains the anthranilamide compound, the $C_{8-12}$ polyoxyethylene alkyl aryl ether, the polyoxyethylene tristyrylphenyl ether, the $C_{8-12}$ alkylbenzene sulfonate and the N,N-dimethylacetamide.

(5) The composition according to the above (3), which contains the anthranilamide compound, the polyoxyethylene tristyrylphenyl ether, the $C_{8-12}$ alkylbenzene sulfonate and cyclohexanone.

(6) The composition according to the above (3), which contains the anthranilamide compound, the polyoxyethylene tristyrylphenyl ether, the $C_{8-12}$ alkylbenzene sulfonate, N,N-dimethylacetamide and γ-butyrolactone.

(7) The composition according to the above (3), which contains the anthranilamide compound, the $C_{8-18}$ polyoxyethylene alkyl ether phosphoric acid ester and N,N-dimethylacetamide.

(8) A composition which contains an anthranilamide compound; as a dispersant, a nonionic surfactant and/or an anionic surfactant; at least one hydrophilic organic solvent selected from the group consisting of N,N-dimethylacetamide, dimethylsulfoxide, γ-butyrolactone, N-methyl-2-pyrrolidone and cyclohexanone; and polyvinylpyrrolidone.

(9) The composition according to the above (8), which contains from 0.1 to 45 wt % of the anthranilamide compound, from 0.1 to 40 wt % of the dispersant, from 99.7 to 15 wt % of the hydrophilic organic solvent and from 0.1 to 20 wt % of polyvinylpyrrolidone.

The composition of the present invention is usually diluted from 5 to 100,000 times, preferably from 50 to 10,000 times, with water for use.

By diluting the composition of the present invention with water, the water-insoluble anthranilamide compound particles precipitate, and uniform suspended spray liquid is prepared.

The average particle size of the anthranilamide compound to be precipitated by diluting the composition of the present invention with water is from 0.01 to 50 μm, preferably from 0.1 to 10 μm.

Further, the crystal state of the particles to be precipitated may be crystalline or non-crystalline, or a mixture thereof.

The composition of the present invention can be prepared by dissolving the compound of the formula (I) and the dispersant in the hydrophilic organic solvent.

Now, the present invention will be described with reference to Examples, but it should be understood that the present invention is by no means restricted thereto.

Further, the constituting components of the dispersants used in Examples are as shown below.

Sorpol 2806B: A mixture of polyoxyethylene tristyrylphenyl ether, polyoxyethylene alkyl aryl ether, alkyl aryl sulfonate, etc.
SORPOL T-20: Polyoxyethylene tristyrylphenyl ether
RHODACAL 60BE: Calcium alkylbenzene sulfonate
PLYSURF A-208B: Polyoxyethylene alkyl ether phosphoric acid ester
SOPROPHOR FLK/70: Potassium polyoxyethylene tristyrylphenyl ether phosphoric acid ester

EXAMPLES

Example 1

5.2 g of the compound (1) and 5 g of SORPOL 2806B (manufactured by Toho Chemical Industry Co., Ltd.) were dissolved in 89.8 g of N,N-dimethylacetamide, to obtain 100 g of a transparent liquid composition containing 5 wt % of the compound (1).

Example 2

5.3 g of the compound (1), 5 g of SORPOL T-20 (manufactured by Toho Chemical Industry Co., Ltd.) and 5 g of RHODACAL 60BE (manufactured by Rhodia Nikka) were dissolved in 84.7 g of cyclohexanone, to obtain 100 g of a transparent liquid composition containing 5 wt % of the compound (1).

Example 3

10.6 g of the compound (1), 0.35 g of SORPOL T-20 and 0.15 g of RHODACAL 60BE were dissolved in 30 g of N,N-dimethylacetamide and 58.9 g of γ-butyrolactone, to obtain 100 g of a transparent liquid composition containing 10 wt % of the compound (1).

Example 4

10.6 g of the compound (1) and 1.0 g of PLYSURF A-208B were dissolved in 88.7 g of N,N-dimethylacetamide, to obtain 100 g of a transparent liquid composition containing 10 wt % of the compound (1).

Example 5

10.6 g of the compound (1), 10.5 g of SORPOL T-20 and 4.5 g of RHODACAL 60BE were dissolved in 10 g of N,N-dimethylacetamide and 64.4 g of γ-butyrolactone, to obtain 100 g of a transparent liquid composition containing 10 wt % of the compound (1).

Example 6

10.6 g of the compound (1), 1 g of PLYSURF A-208B and 10.0 g of polyvinylpyrrolidone K-30 (manufactured by Nacalai Tesque, Inc.) were dissolved in 78.4 g of N,N-dimethylacetamide, to obtain 100 g of a transparent liquid composition containing 10 wt % of the compound (1).

Comparative Example 1

Zirconia beads were added a mixture of 2.1 g of the compound (1), 4 g of propylene glycol, 1.2 g of SOPROPHOR FLK/70 (manufactured by Rhodia Nikka), 0.4 g of Veegum (anti-setting agent, manufactured by Sanyo Chemical Industries, Ltd.), 0.2 g of RHODOSIL 432 (antifoaming agent, manufactured by Rhodia Nikka) and 32.1 g of water, and the mixture was pulverized by a wet pulverizing machine (DYNO-MILL: KDL type, manufactured by Shinmaru Enterprises Corporation) for 16 minutes, followed by removing beads by filtration, to obtain a concentrated suspended liquid containing 5 wt % of the compound (1).

Test Example 1

Efficacy Against Silverleaf Whitefly (*Bemisia argentifoli*)

(1) Preparation of Sample Solutions

Compositions obtained in Example 1 and Comparative Example 1 were diluted 1,000 times with water respectively to prepare 50 ppm test liquids of compound (1), and the respective test liquids were diluted 2 times, 4 times and 16 times with water to prepare 25 ppm, 12.5 ppm and 3.1 ppm test liquids. The respective test liquids were suspended solutions in which fine solid particles were uniformly dispersed.

(2) Efficacy Test

Adults of silverleaf whitefly were released on cucumber with only one first true leaf left and other leaves cut off and planted in a pot, and permitted to lay eggs for about 24 hours. Thereafter, the pot was left for 9 days in a constant temperature chamber at 25° C. with lightening. The number of hatchlings was counted, and then, the test liquid of 12.5 or 3.1 ppm was sprayed uniformly on the leaf by a hand spray. After the treatment, the pot was left in a constant temperature chamber at 25° C. with lightening for 10 days, whereupon the number of old instar larvae and the number of pupae were counted, and the controlling value was obtained by the following equation. Table 1 shows the test results. From Table 1, it is evident that the controlling effect of the formulation of the present invention is superior to that of Comparative Example.

$$\text{Controlling value (\%)} = (1 - ((Ta \times Cb)/(Tb \times Ca))) \times 100$$

Ta: The number of old instar larvae+the number of pupae after the treatment at the treated section Tb: The number of hatchlings before the treatment at the treated section Ca: The number of old instar larvae+the number of pupae after the treatment at untreated section Cb: the number of hatchling before the treatment at the untreated section

TABLE 1

| | Controlling value (%) | |
|---|---|---|
| | 12.5 ppm | 3.1 ppm |
| Example 1 | 100 | 99 |
| Comparative Example 1 | 50 | 43 |

Test Example 2

Efficacy Against Silverleaf Whitefly (*Bemisia argentifoli*) (Greenhouse Test)

Eggplants (from 9 to 10 leaf stage) planted in a pot having a diameter of 18 cm were left for 14 days in a greenhouse in which adults of silverleaf whitefly inhabited. Then, each one leaf disk having a diameter of 2 cm was obtained from three leaves, and the numbers of eggs, larvae and pupae were counted. Next day, 80 ml of test solution at 50 or 25 ppm prepared in the same manner as in Test Example 1 was sprayed by a compressed air type sprayer (KZ-2, manufactured by Sakata.) so that the surface of the eggplant could be wet by test solution uniformly, and then treated plants were put in is greenhouse. After two weeks, leaf disks were obtained in the same manner as in the assessment before the treatment, and the numbers of eggs, larvae and pupae were counted. The controlling value was obtained by the following equation. The test was conducted with two replications. Table 2 shows the test results. From Table 2, it is evident that the controlling effect of the formulation of the present invention is superior to that of Comparative Example.

$$\text{Controlling value (\%)} = (1 - ((Ta \times Cb)/(Tb \times Ca))) \times 100$$

Ta: The number of middle-stage larvae+the number of old larvae+the number of pupae at the treated section after two weeks from the treatment Tb: The number of young larvae+the number of eggs at the treated section before the treatment Ca: The number of middle-stage larvae+the number of old larvae+the number of pupae at the untreated section after two weeks from the treatment Cb: The number of young larvae+the number of eggs at the untreated section before the treatment

TABLE 2

| | Controlling value (%) | |
|---|---|---|
| | 50 ppm | 25 ppm |
| Example 1 | 96 | 98 |
| Comparative Example 1 | 34 | 12 |

Test Example 3

Efficacy Against Western Flower Thrips (*Frankliniella occidentalis*) (Greenhouse Test)

The adults and larvae of western flower thrips which infested on eggplants (from 8 to 9 leaf stage) planted in a pot having a diameter of 18 cm was counted. Next day, 90 ml of test solution at 50 ppm prepared in the same manner as in test Example 1 was sprayed by a compressed air type sprayer (KZ-2, manufactured by Sakata.) so that the surface of the eggplant could be wet by test solution uniformly, and then the treated plants were put in greenhouse. After 12 days, the same assessment before the treatment was carried out, and the controlling value was obtained by the following equation. Table 3 shows the test results. From Table 3, it is evident that the controlling effect of the formulation of the present invention is superior to that of Comparative Example.

$$\text{Controlling value (\%)} = (1 - ((Ta \times Cb)/(Tb \times Ca))) \times 100$$

Ta: The number of adults+the number of larvae at the treated section after 12 days from the treatment Tb: The number of adults+the number of larvae at the treated section before the treatment Ca: The number of adults+the number of larvae at the untreaetd section after 12 days from the treatment Cb: The number of adults+the number of larvae at the untreated section before the treatment

TABLE 3

| | Controlling value (%) 50 ppm |
|---|---|
| Example 1 | 85 |
| Comparative Example 1 | 33 |

The entire disclosures of Japanese Patent Application No. 2008-063782 filed on Mar. 13, 2008 and Japanese Patent Application No. 2008-305084 filed on Nov. 28, 2008 including specifications, claims and summaries are incorporated herein by reference in their entireties.

The invention claimed is:

1. A pesticide composition, comprising, based on a total weight of the composition:
   (i) from 0.1 to 45 wt % of an anthranilamide compound of formula (I):

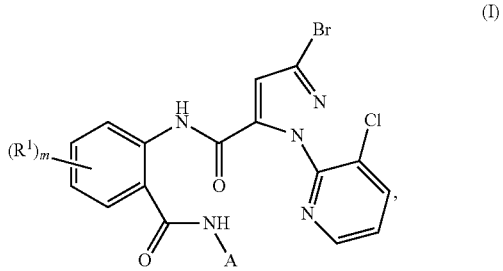

wherein:
   R' is halogen, alkyl, or cyano;
   A is alkyl which is optionally substituted with $C_{3-4}$ cycloalkyl; and
   m is from 0 to 4;
   (ii) from 0.1 to 40 wt % of a dispersant; and
   (iii) from 99.8 to 15 wt % of a hydrophilic organic solvent selected from the group consisting of N,N-dimethylacetamide, dimethylformamide, dimethylsulfoxide, cyclohexanone, γ-butyrolactone, N-methyl-2-pyrrolidone, N-octyl-2-pyrrolidone, N-dodecyl-2-pyrrolidone, tetrahydroxyfurfuryl alcohol, and propylene glycol monomethyl ether,
   wherein the anthranilamide compound and the dispersant are dissolved in the hydrophilic organic solvent, and
   wherein when the composition is diluted with water, the anthranilamide compound uniformly precipitates as fine solid particles in water.

2. The composition of claim 1, wherein the anthranilamide compound is:
   (a) 3-bromo-N-(2-bromo-4-chloro-6-(1-cyclopropylethylcarbamoyl)phenyl)-1-(3-chloropyridin-2-yl)-1H-pyrazol-5-carboxamide;
   (b) 3-bromo-N-(4-chloro-2-(1-cyclopropylethylcarbamoyl)-6-methylphenyl)-1-(3-chloropyridin-2-yl)-1H-pyrazol-5-carboxamide;
   (c) 3-bromo-N-(2-bromo-4-chloro-6-(cyclopropylmethylcarbamoyl)phenyl)-1-(3-chloropyridin-2-yl)-1H-pyrazol-5-carboxamide;
   (d) 3-bromo-N-(4-chloro-2-methyl-6-(methylcarbamoyl)phenyl)-1-(3-chloropyridin-2-yl)-1H-pyrazol-5-carboxamide; or
   (e) 3-bromo-1-(3-chloropyridin-2-yl)-N-(4-cyano-2-methyl-6-(methylcarbamoyl)phenyl-1H-pyrazol-5-carboxamide.

3. The composition of claim 1, wherein the hydrophilic organic solvent is at least one selected from the group consisting of N,N-dimethylacetamide, dimethylsulfoxide, γ-butyrolactone, N-methyl-2-pyrrolidone and cyclohexanone.

4. The composition of claim 1, wherein the dispersant is a nonionic surfactant and/or an anionic surfactant.

5. The composition of claim 1, wherein the dispersant is at least one selected from the group consisting of a $C_{8-12}$ polyoxyethylene alkyl aryl ether, a polyoxyethylene tristyrylphenyl ether, a $C_{8-12}$ alkylbenzene sulfonate and a $C_{8-18}$ polyoxyethylene alkyl ether phosphoric acid ester.

6. The composition of claim 1, comprising:
   (i) the anthranilamide compound;
   (ii) a nonionic surfactant and/or an anionic surfactant as the dispersant; and
   (iii) at least one hydrophilic organic solvent selected from the group consisting of N,N-dimethylacetamide, dimethylsulfoxide, γ-butyrolactone, N-methyl-2-pyrrolidone and cyclohexanone.

7. The composition of claim 1, comprising:
   (i) the anthranilamide compound;
   (ii) at least one dispersant selected from the group consisting of a $C_{8-12}$ polyoxyethylene alkyl aryl ether, a polyoxyethylene tristyrylphenyl ether, a $C_{8-12}$ alkylbenzene sulfonate and a $C_{8-18}$ polyoxyethylene alkyl ether phosphoric acid ester; and
   (iii) at least one hydrophilic organic solvent selected from the group consisting of N,N-dimethylacetamide, dimethylsulfoxide, γ-butyrolactone, N-methyl-2-pyrrolidone and cyclohexanone.

8. The composition of claim 1, wherein the content of the anthranilamide compound is from 1 to 20 wt %, based on a total weight of the composition.

9. The composition of claim 1, wherein the content of the dispersant is from 0.5 to 20 wt %, based on a total weight of the composition.

10. The composition of claim 8, wherein the content of the dispersant is from 0.5 to 20 wt %, based on a total weight of the composition.

11. The composition of claim 1, wherein the average particle size of the fine solid particles is from 0.01 to 50 μm.

* * * * *